United States Patent [19]

Patsch

[11] Patent Number: 5,625,089
[45] Date of Patent: Apr. 29, 1997

[54] ANILINE DERIVATIVES

[75] Inventor: Manfred Patsch, Wachenheim, Germany

[73] Assignee: BASF Aktiengesellschaft, Ludwigshafen, Germany

[21] Appl. No.: 608,198

[22] Filed: Feb. 28, 1996

[30] Foreign Application Priority Data

Mar. 9, 1995 [DE] Germany ............... 195 08 311.3

[51] Int. Cl.$^6$ .................. C07C 305/24; C07C 317/14
[52] U.S. Cl. .............. 558/26; 546/264; 558/33; 560/12; 562/46; 562/47; 562/58; 562/59; 562/65; 564/85; 564/86; 564/168; 564/283; 564/284; 564/288; 564/290; 564/328; 564/428; 564/430
[58] Field of Search ............... 546/264; 558/26, 558/33; 560/12; 562/58; 564/85, 86, 168, 283, 328, 428, 430

[56] References Cited

U.S. PATENT DOCUMENTS 3,008,950  11/1961  Heyna et al. ............... 564/168 X

OTHER PUBLICATIONS

Shimanoki et al., Chemical Abstract, vol. 117, abstract 113673. 1992.
Shimanoki et al., Chemical Abstracts, vol. 117, abstract 113668. 1992.

Primary Examiner—Richard L. Raymond
Attorney, Agent, or Firm—Oblon, Spivak, McClelland, Maier & Neustadt, P.C.

[57] ABSTRACT

Anilines of the formula

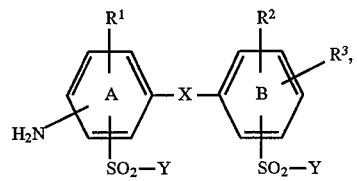

where rings A and B may each be benzofused,

X is a bridge member, $R^1$ and $R^2$ are each hydrogen, $C_1$–$C_4$-alkyl, $C_1$–$C_4$-alkoxy, halogen, hydroxysulfonyl, carboxyl, $C_1$–$C_4$-alkoxycarbonyl or $C_1$–$C_4$-alkylsulfonyl, $R^3$ is hydrogen, amino, $C_1$–$C_4$-alkanoylamino or nitro, and Y is vinyl or a radical of the formula $C_2H_4$—Q, where Q is a group detachable under alkaline reaction conditions.

6 Claims, No Drawings

ANILINE DERIVATIVES

The present invention relates to novel anilines of the formula I

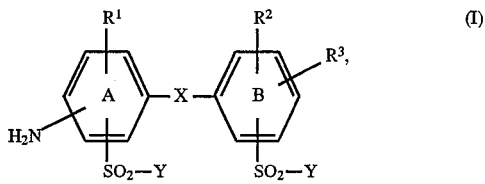

where
rings A and B may each be benzofused,
  is a radical of the formula CO, SO$_2$, CONZ or SO$_2$NZ, where Z is in each case hydrogen or C$_1$–C$_4$-alkyl,
R$^1$ and R$^2$ are each independently of the other hydrogen, C$_1$–C$_4$-alkyl, C$_1$–C$_4$-alkoxy, halogen, hydroxysulfonyl, carboxyl,
C$_1$–C$_4$-alkoxycarbonyl or C$_1$–C$_4$-alkylsulfonyl,
R$^3$ is hydrogen, amino, C$_1$–C$_4$-alkanoylamino or nitro, and
Y is vinyl or a radical of the formula C$_2$H$_4$—Q, where Q is a group detachable under alkaline reaction conditions.

It is an object of the present invention to provide novel aniline derivatives which are simple to prepare and useful as dye intermediates.

We have found that this object is achieved by the above-described anilines of the formula I.

Any alkyl appearing in the abovementioned formula I may be straight-chain or branched.

Z, R$^1$ and R$^2$ are each for example methyl, ethyl, propyl, isopropyl, butyl, isobutyl, sec-butyl or tert-butyl.

R$^1$ and R$^2$ may each also be for example methoxy, ethoxy, propoxy, isopropoxy, butoxy, isobutoxy, sec-butoxy, fluorine, chlorine, bromine, methoxycarbonyl, ethoxycarbonyl, propoxycarbonyl, isopropoxycarbonyl, butoxycarbonyl, methylsulfonyl, ethylsulfonyl, propylsulfonyl, isopropylsulfonyl or butylsulfonyl.

R$^3$ is for example formylamino, acetylamino, propionylamino, butyrylamino or isobutyrylamino.

Q is a group detachable under alkaline reaction conditions. Examples of such groups are chlorine, bromine, C$_1$–C$_4$-alkylsulfonyl, phenylsulfonyl, OSO$_3$H, SSO$_3$H, OP(O)(OH)$_2$, C$_1$–C$_4$-alkylsulfonyloxy, phenylsulfonyloxy, C$_1$–C$_4$-alkanoyloxy, C$_1$–C$_4$-dialkylamino or a radical of the formula

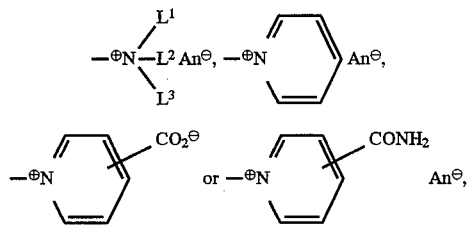

where L$^1$, L$^2$ and L$^3$ are each independently of the other C$_1$–C$_4$-alkyl or benzyl and An$^\ominus$ is in each case an equivalent of an anion. Examples of suitable anions are fluoride, chloride, bromide, iodide, mono-, di- or trichloroacetate, methanesulfonate, benzenesulfonate and 2- or 4-methylbenzenesulfonate.

When the anilines of the formula I contain hydroxysulfonyl and/or carboxyl groups, it will be appreciated that the claims encompass not only the free acids but also the salts thereof.

Suitable cations are derived from metal or ammonium ions. Metal ions are in particular the lithium, sodium or potassium ions. Ammonium ions for the purpose of the present invention are substituted or unsubstituted ammonium cations. Examples of substituted ammonium cations are monoalkyl-, dialkyl-, trialkyl-, tetraalkyl- or benzyltrialkyl-ammonium cations or those cations which are derived from nitrogenous five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl is generally to be understood as meaning straight-chain or branched C$_1$–C$_{20}$-alkyl which may be substituted by hydroxyl groups and/or interrupted by from 1 to 4 oxygen atoms in ether function.

Preference is given to anilines of the formula I where said rings A and B are each not benzofused.

Preference is further given to anilines of the formula I where L is a radical of the formula CO, SO$_2$, CONH or SO$_2$NH.

Preference is further given to anilines of the formula I where R$^1$ and R$^2$ are each hydrogen.

Preference is further given to anilines of the formula I where R$^3$ is hydrogen, amino or acetylamino.

Preference is further given to anilines of the formula I where, in ring A, the amino group and the SO$_2$—Y radical are ortho to each other.

Particular preference is given to anilines of the formula Ia

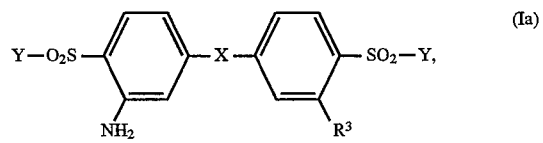

where
X is a radical of the formula CO, SO$_2$ or SO$_2$NH,
R$^3$ is hydrogen or amino, and
Y is as defined above.

The anilines of the formula I according to the present invention can be prepared in a conventional manner.

For example, a halogen compound of the formula II

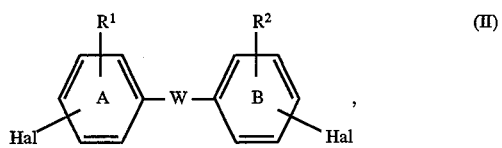

where Hal is in each case halogen, preferably chlorine, and W is a radical of the formula CO or SO$_2$, and R$^1$ and R$^2$ and also the rings A and B are each as defined above, can be nitrated in a conventional manner and the resulting nitro compound of the formula III

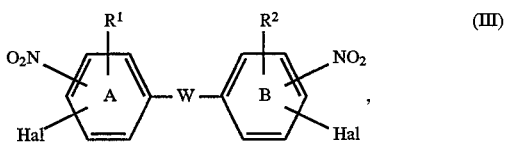

where Hal, R$^1$ R$^2$ W and the rings A and B are each as defined above, reacted with 2-thioethanol to form the compound of the formula IV

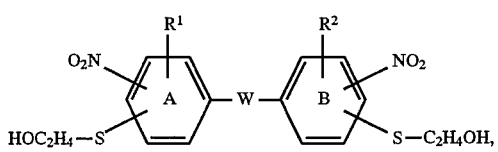 (IV)

where $R^1$, $R^2$ W and the rings A and B are each as defined above.

Said compound IV can then be converted into those novel anilines of the formula I where X is a radical of the formula CO or $SO_2$ by reducing the nitro group to an amino group, oxidizing the sulfur atom to a sulfonyl group and converting the radical $C_2H_4OH$ into the above-defined group Y, which steps can be carried out in any order.

Those anilines of the formula I where X is a radical of the formula CONZ or $SO_2NZ$ can be obtained for example by reacting the acid halides of the formula V

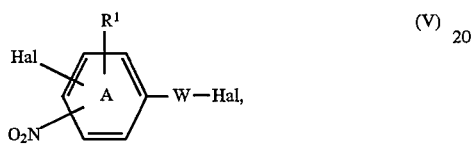 (V)

where Hal, $R^1$ W and the ring A are each as defined above, with amines of the formula VI

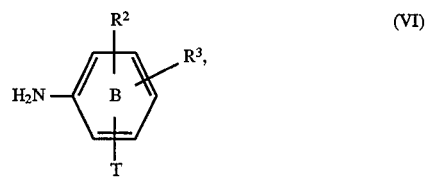 (VI)

where $R^2$, $R^3$ and the ring B are each as defined above and T is 2-hydroxyethylthio or the abovementioned radical $SO_2$-Y, and subsequent reduction of the nitro group to an amino group, oxidation of the sulfur atom to a sulfonyl group and conversion of the radical $C_2H_4OH$ into the above-defined group Y, in which case the last three steps can in turn be carried out in any order.

The novel anilines of the formula I are useful intermediates for dyes, especially reactive dyes.

The Examples which follow illustrate the invention.

EXAMPLE 1

546 g of 2-mercaptoethanol and 336 g of sodium bicarbonate were added to 997 g of 4,4'-dichloro-3,3'-dinitrobenzophenone in 3000 ml of butanol, and the mixture was heated at 110° C. for 12 hours. After cooling the resulting precipitate was filtered off with suction. Washing with isopropanol and subsequently with hot water and drying in a vacuum drying cabinet gave 798 g of 4,4'-bis(2-hydroxyethylmercapto)-3,3'-dinitrobenzophenone. Melting point: 193°–197° C.

EXAMPLE 2 a) 212 g of the compound of Example 1 were dissolved in a mixture of 2500 ml of isopropanol and 1000 ml of water. 50 ml of glacial acetic acid and 5 g of palladium on carbon were added and hydrogen gas was introduced at from 40° to 50° C. When the uptake of hydrogen had ceased, the catalyst was filtered off and the mother liquor was concentrated in a rotary evaporator to isolate 180 g of a brown oil.

b) 36.4 g of the oil obtained under a) were reacted with 25 g of acetic anhydride in 50 ml of acetone and 50 ml of water at from 45° to 50° C. After addition of 1 g of tungstic acid, 48 g of 30% strength by weight aqueous hydrogen peroxide were added dropwise over 3 hours. Concentrating and recrystallizing from butanol yielded 25 g of 4,4'-bis-(2-hydroxyethylsulfonyl)-3,3'-bisacetylaminobenzophenone. Melting point: 189°–192° C.

EXAMPLE 3

180 g of the compound of Example 2b) were heated at 100° C. for 2 hours in 200 ml of 20% strength by weight hydrochloric acid. The batch was poured onto 1000 ml of water, and dilute sodium hydroxide solution was added to pH 6. A brown oil separated. Drying yielded 120 g of 4,4'-bis(2-hydroxyethylsulfonyl)-3,3'-diaminobenzophenone.

EXAMPLE 4

75 g of the compound of Example 3 were added to 500 g of 5% strength by weight oleum at from 15° to 20° C., and the mixture was stirred for a further 24 hours. It was then diluted with water to 1200 g. A precipitate formed and was filtered off with suction to isolate 91 g of the compound of the formula

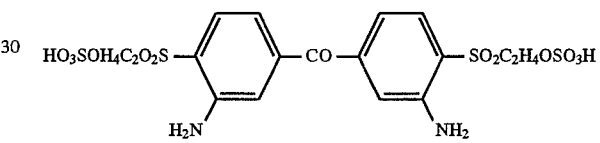

Melting point: 203°–105° C.

EXAMPLE 5

The method of Examples 1 to 4 was repeated using as starting material an equivalent amount of 4,4'-dichloro-3,3'-dinitrodiphenyl sulfone, affording via the intermediate stages of the formula

| $E^1$ | $E^2$ | mp. |
|---|---|---|
| $SC_2H_4OH$ | $NO_2$ | 296–300° C. |
| $SC_2H_4OH$ | $NH_2$ | oil |
| $SO_2C_2H_4OH$ | $NHCOCH_3$ | 206–210° C. |
| $SO_2C_2H_4OH$ | $NH_2$ | 234–237° C. | the product where $E^1=SO_2C_2H_4OSO_3H$ and $E^2=NH_2$ (mp>230° C. dec.).

EXAMPLE 6

285 g of 3-nitro-4-chlorobenzenesulfonyl chloride and 242 g of 4-(2-hydroxyethylsulfonyl)aniline were stirred in 750 ml of water at pH 6.5 at 40° C. for six hours. The precipitate was filtered off with suction. Drying yielded 480 g of the compound of the formula

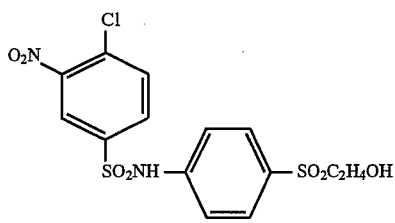

Melting point: 147°–152° C.

EXAMPLE 7

430 g of the compound from Example 6 were refluxed for 6 hours in 750 ml of isobutanol together with 77 g of 2-mercaptoethanol and 84 g of sodium bicarbonate. 370 g were isolated of the compound of the formula

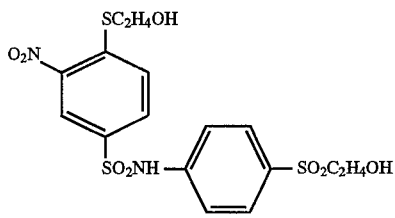

NMR (D$_6$-DMSO): 3.20(M,2), 3.35(M,2), 3.69(M,4)~5.0 (br.S,2), 7.28(D,2), 7.73(D,2), 7.86(D,1), 8.02(D,1), S.5S(D,1).

EXAMPLE 8 a) 370 g of the compound of Example 7 in a mixture of 1000 ml of water, 1000 ml of isopropanol and 500 ml of glacial acetic acid were admixed with 113 g of iron powder at from 60° to 65° C. The temperature rose to 80° C. in the course of the addition. After clarification the solvent was distilled off under reduced pressure, leaving 205 g of a brown oil.

b) 172 g of the compound described under a) in 200 ml of water were admixed with 100 ml of acetic anhydride at from 40° to 30° C. After stirring at from 60° to 65° C. for three hours the batch was poured onto 200 ml of water, 0.5 g of tungstic acid was added, and 91 g of 30% strength by weight hydrogen peroxide were added dropwise at from 60° to 65° C. The resulting precipitate was filtered off with suction to yield 116 g of the compound of the formula

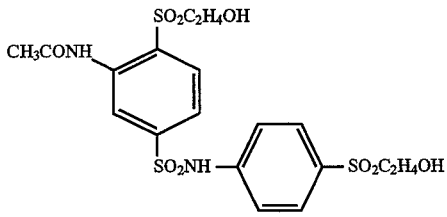

Melting point: 134°–136° C.

c) Deacetylation and formation of the bishydrogensulfate took place in concentrated sulfuric acid at from 35° to 40° C. Dilution onto ice afforded a solution of the compound of the formula

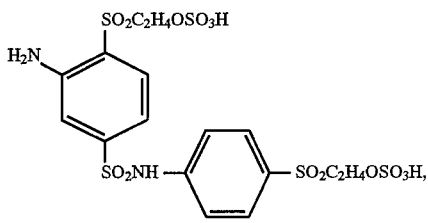

which can be used directly for dye synthesis.

We claim:

1. Anilines of the formula I

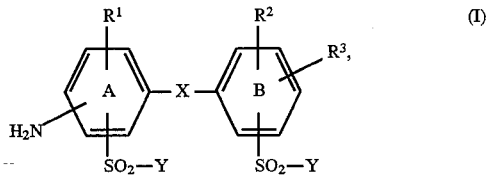

where rings A and B may each be benzofused,

X is a radical of the formula CO, SO$_2$, CONZ or SO$_2$NZ, where Z is in each case hydrogen or C$_1$–C$_4$-alkyl, R$^1$ and R$^2$ are each independently of the other hydrogen, C$_1$–C$_4$-alkyl, C$_1$–C$_4$-alkoxy, halogen, hydroxysulfonyl, carboxyl, C$_1$–C$_4$-alkoxycarbonyl or C$_1$–C$_4$-alkylsulfonyl, R$^3$ is hydrogen, amino, C$_1$–C$_4$-alkanoylamino or nitro, and Y is vinyl or a radical of the formula C$_2$H$_4$—Q, where Q is a group detachable under alkaline reaction conditions.

2. Anilines as claimed in claim 1, wherein said rings A and B are each not benzofused.

3. Anilines as claimed in claim 1, wherein X is a radical of the formula CO, SO$_2$, CONH or SO$_2$NH.

4. Anilines as claimed in claim 1, wherein R$^1$ and R$^2$ are each hydrogen.

5. Anilines as claimed in claim 1, wherein R$^3$ is hydrogen, amino or acetylamino.

6. Anilines as claimed in claim 1, wherein, in ring A, the amino group and the SO$_2$-Y radical are ortho to each other.

* * * * *